(12) United States Patent
Swain et al.

(10) Patent No.: US 7,879,051 B2
(45) Date of Patent: Feb. 1, 2011

(54) FLEXIBLE DEVICE FOR TRANSFIXING AND JOINING TISSUE

(76) Inventors: Christopher Paul Swain, 41 Willow Road, London NW3 1TN (GB); Charles Alexander Mosse, 21 Parliment Mill, London NW3 3TA (GB)

(*) Notice: Subject to any disclaimer, the term of this patent is extended or adjusted under 35 U.S.C. 154(b) by 676 days.

(21) Appl. No.: 10/477,762

(22) PCT Filed: May 20, 2002

(86) PCT No.: PCT/GB02/02168
§ 371 (c)(1),
(2), (4) Date: Apr. 30, 2004

(87) PCT Pub. No.: WO02/094108
PCT Pub. Date: Nov. 28, 2002

(65) Prior Publication Data
US 2004/0186514 A1 Sep. 23, 2004

(30) Foreign Application Priority Data
May 18, 2001 (GB) ................................. 0112250.6
May 18, 2001 (GB) ................................. 0112252.2

(51) Int. Cl.
*A61B 17/08* (2006.01)
(52) U.S. Cl. .................................................. 606/153
(58) Field of Classification Search ................. 606/224, 606/144, 145, 148, 153, 154–156, 225–227, 606/232; 600/12
See application file for complete search history.

(56) References Cited

U.S. PATENT DOCUMENTS

| | | | |
|---|---|---|---|
| 2,701,559 A | 1/1955 | Cooper | |
| 3,986,493 A * | 10/1976 | Hendren, III | 600/12 |
| 4,741,330 A | 5/1988 | Hayhurst | |
| 4,907,591 A * | 3/1990 | Vasconcellos et al. | 606/154 |
| 5,041,085 A * | 8/1991 | Osborne et al. | 604/541 |
| 5,041,129 A | 8/1991 | Hayhurst et al. | |
| RE34,021 E * | 8/1992 | Mueller et al. | 604/533 |

(Continued)

FOREIGN PATENT DOCUMENTS

WO    WO 01/12074 A1    2/2001

OTHER PUBLICATIONS

"Anastomosis at flexible endoscopy: and experimental study of compression button gastrojejunostomy", C. Swain, et al, Gastrointestinal Endoscopy, 2 pages, XP009001157.

*Primary Examiner*—Todd E Manahan
*Assistant Examiner*—Lindsey Bachman
(74) *Attorney, Agent, or Firm*—Blakely, Sokoloff, Taylor & Zafman (57) ABSTRACT

A surgical device is provided for use in joining a first tissue layer forming a first hollow region and a second tissue layer forming a wall of a second hollow region, to produce an anastomosis. The device comprises a needle capable of passing from the first region to the second region by penetrating the tissue layers, a tag removably carried by the needle, the tag having a trailing portion, and means for separating the tag from the needle after the needle has penetrated both layers, to leave the tag in the second hollow region, but with the trailing portion extending into the first hollow region. Anastomosis forming articles are described which comprise a pair of components for compressing the tissue layers between them.

12 Claims, 12 Drawing Sheets

U.S. PATENT DOCUMENTS

| | | | |
|---|---|---|---|
| 5,449,368 A * | 9/1995 | Kuzmak | 606/157 |
| 5,476,469 A * | 12/1995 | Hathaway et al. | 606/144 |
| 5,626,614 A * | 5/1997 | Hart | 606/232 |
| 5,690,656 A * | 11/1997 | Cope et al. | 606/153 |
| 5,817,113 A * | 10/1998 | Gifford et al. | 606/153 |
| 5,868,708 A | 2/1999 | Hart et al. | |
| 5,954,732 A * | 9/1999 | Hart et al. | 606/144 |
| 6,063,114 A * | 5/2000 | Nash et al. | 623/1.36 |
| 6,491,707 B2 * | 12/2002 | Makower et al. | 606/157 |
| 6,500,184 B1 * | 12/2002 | Chan et al. | 606/144 |
| 6,508,777 B1 * | 1/2003 | Macoviak et al. | 604/4.01 |
| 6,699,233 B2 * | 3/2004 | Slanda et al. | 604/533 |
| 6,699,263 B2 * | 3/2004 | Cope | 606/232 |

* cited by examiner

FLEXIBLE DEVICE FOR TRANSFIXING AND JOINING TISSUE

The present patent application is a non-provisional application of International Application No. PCT/GB02/01268, filed May 20, 2002.

FIELD OF THE INVENTION

This invention relates to methods and devices for transfixing and joining tissues and, more particularly, to forming anastomoses.

BACKGROUND OF THE INVENTION

In abdominal and vascular surgery anastomosis, the joining together of hollow structures, is an important goal. The ability to establish continuity between two hollow structures can relieve blockage due to cancer, inflammation or other pathology, can allow the removal of abnormal tissue or organs, and, by bypassing a blocked segment, can allow the unimpeded movement of food or facilitate the flow of blood or bile through the body.

Anastomoses are most commonly formed at open abdominal surgery (laparotomy). Hand sewn anastomoses, usually in two or even three layers, are widely performed but are time consuming and require large incisions for hand access. Stapled anastomoses became widely performed especially in colonic surgery since they allowed surgeons to remove low rectal tumours. The short rectal remnant could be joined to the colon above the tumour at a site where it was difficult to place stitches by hand, and in consequence allowed patients to recover without needing a permanent colostomy. The advent of laparoscopic surgery staplers allowed anastomoses to be formed through incisions of 1-2 cm or so that were just large enough to allow passage of these instruments inside the abdominal or thoracic cavity.

Some aids to form anastomoses have been developed. J. B. Murphy, an American surgeon working in Chicago in the 1880's, popularized surgical anastomoses by creating a compression button device for anastomosis. The device had two mushroom-shaped buttons, which could be placed in the two organs to be joined. The buttons could be pressed together by an internal spring in the stalk of the mushroom and the organs would be welded together by the consequent ischaemia (lack of blood supply) at the sites where the buttons were pressed together. Eventually the button device would fall through into the gut, leaving an anastomosis or hole and be passed through the body into the toilet. Compression button anastomoses are still used at open colonic surgery. The use of magnets to compress tissue to form an anastomosis has also been described, and a spring compression button method using a biofragmentable ring has been employed, especially in the rectum.

An anastomosis procedure has been described in an article entitled "Anastomosis at Flexible Endoscopy: an experimental study of compression button gastrojejunoscopy", P Swain and N Mills, Gastrointestinal Endoscopy 1991, 37: 625-631, in which, as its title implies, a method is described of forming anastomoses using a flexible endoscope. The method described there involved introducing a flexible endoscope into one of the two structures to be joined (in this case the stomach), and entering the second of the two structures (in this case the small bowel) by forming an incision in the abdomen of the subject. The present invention is directed, in one aspect thereof, to the formation of anastomoses without the need to make such external incisions, though in other aspects thereof the means described herein which make this possible are applied to anastomoses in the formation of which such incisions are made.

The ability to form anastomoses using flexible endoscopic or percutaneous procedures without opening the abdomen or chest or using laparoscopic methods might offer advantages especially to patients with advanced cancer or in elderly or sick patients, who might withstand conventional surgery poorly. In particular, flexible endoscopy might allow anastomoses to be formed from stomach to small bowel, duodenum to gallbladder, and small bowel to colon.

Flexible endoscopy allows access to many hollow organs including oesophagus, stomach, duodenum, small intestine and colon, and most flexible endoscopes have a channel through which instruments can be passed. Although the flexible endoscopes employed for most conventional purposes do not provide information on the location of tubular structures outside the organ, modified flexible endoscopes employing ultrasound are available which do. Endoscopic ultrasound is a hybrid method, which uses ultrasound imaging at the tip of the endoscope but retains the optical imaging and internal instrument channel of a conventional endoscope. Some such endoscopes have their imaging array constructed in a linear fashion, which allows good ultrasound visualization of organs adjacent to the organ in which the tip of the endoscope lies.

SUMMARY OF THE INVENTION

Devices are described here which can form anastomoses either through flexible endoscopes or at percutaneous needle access, which do not require surgical incision or laparoscopy (although they might be used during either of these surgical methods to form an anastomosis), and which may be used in combination with ultrasound or x-ray imaging externally to the patient or, preferably, imaging internally to the patient, for example using endoscopic ultrasound.

Accordingly to the present invention there is provided a surgical device for use in joining a first tissue layer forming a wall of a first hollow region and a second tissue layer forming a wall of a second hollow region, the device comprising a needle capable of passing from the first region to the second region by penetrating the said tissue layers, a tag removably carried by the needle, the tag having a trailing portion, and the tag being separable from the needle after the needle has penetrated both layers, to leave the tag in the second region, but with the said trailing portion extending into the first region. The trailing portion is preferably a thread or wire, with the tag being free to tilt with respect thereto, after the tag has entered the second region.

The invention further provides a method of surgery which may employ the above surgical device. In further aspects thereof the invention additionally provides various entities which may be used in carrying out the surgical method, some of which may be capable of use in surgery not employing the above mentioned tag. Also, it is within the scope of the invention to use some of the ideas disclosed herein outside the field of anastomosis formation.

According to another aspect of the present invention there is provided an element of a device for forming an anastomosis, which element comprises a hollow sheath, and an elongate carrier member passing through the hollow sheath, with a portion of the sheath being attached to the carrier member and the remainder of the sheath being free to move lengthwise with respect to the carrier member, whereby such lengthwise movement causes the sheath to bulge outwardly. Preferably the sheath is a braided sheath, and more preferably it is a braided sheath of a surgically acceptable metal. The portion of the sheath which is attached to the carrier member is preferably at or adjacent one end thereof, and the sheath preferably has a sliding collar at or adjacent its other end to assist the above mentioned lengthwise movement. This aspect of the invention further provides a device for forming an anastomosis which comprises an element as set out above and a further element in the form of a cup for cooperating with the first mentioned element. The cup preferably has an aperture therein for the carrier member to pass through.

In a preferred form, the invention, in its various aspects, relates to the formation of anastomoses.

BRIEF DESCRIPTION OF THE DRAWINGS

The invention is described in more detail below with reference, to the accompanying diagrammatic drawings, in which:

FIGS. 4a to 4e show successive stages in forming an anastomosis using, as one apparatus component, the device shown in FIGS. 3a and 3b.

DETAILED DESCRIPTION OF THE INVENTION

Figure 8:
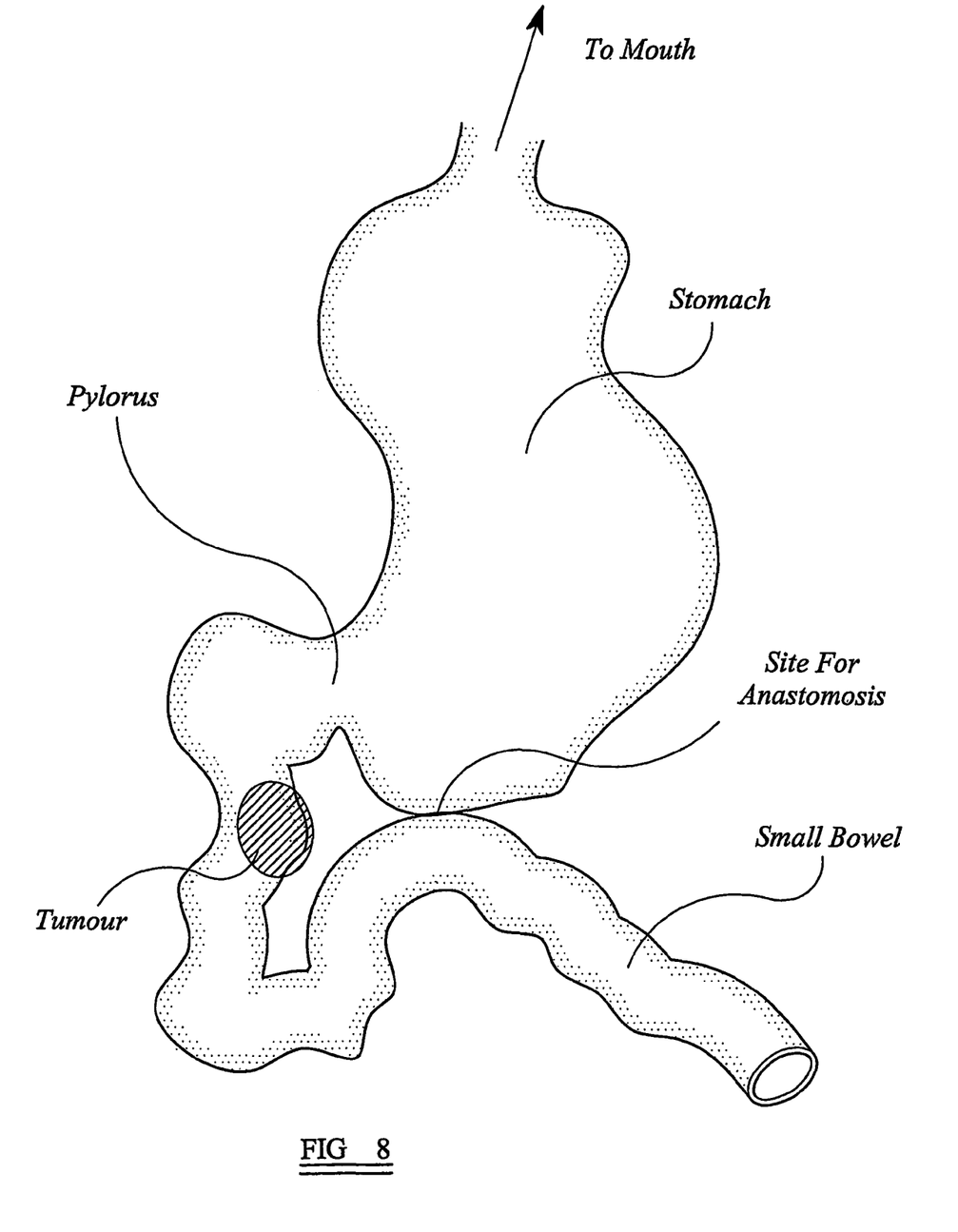
FIG. 8 is a diagram of part of the gastrointestinal tract to assist in understanding the anatomical aspects of what is described below.

Turning first to FIG. 8 of the drawings, it will be seen that this shows part of the gastrointestinal tract, and illustrates a tumour in the upper portion of the small bowel and the site at which it is desired to form an anastomosis to bypass the section of small bowel containing the tumour and thus permit its removal. What will now be described is the use of the embodiment shown in FIGS. 1, 1a, 1b and 2, in conjunction with some known pieces of surgical equipment, to form the anastomosis.

Although there are a number of alternative ways in which the surgical procedure can be carried out, one of them involves the following steps. Firstly a conventional flexible endoscope is passed through the mouth of the patient and thence through the patient's stomach and out through the pylorus into the small bowel. The leading end of the endoscope is passed at least as far as the site of the tumour. If the tumour is small enough it may be possible for the leading end of the endoscope to pass the tumour and reach the site for the anastomosis. If not, the leading end of the endoscope will stop at the tumour, but will need to have the outlet of the relevant channel (for which see below) opposite the gap between the tumour and the opposing small bowel wall. A guide wire is then passed down the biopsy channel of the endoscope until the leading end of the guide wire is located at or adjacent the anastomosis site. At this point there are two alternative possibilities for the next step. One is to remove the endoscope from the patient, leaving the guide wire intact, and thereafter run a balloon catheter down the guide wire until the balloon is at or adjacent the anastomosis site. The alternative is to run the balloon catheter down the guide wire while the guide wire is still in the biopsy channel of the endoscope. In either event, it may be desirable for the balloon catheter to be one which is capable of transmitting torque along its length (such catheters are known for use in cardiology), so as to assist in the passage of the balloon to the desired site. The balloon of the balloon catheter can be inflated at any convenient stage during the forgoing procedure steps, or can be inflated after the step to be described immediately below, namely introducing a flexible ultrasound endoscope. The balloon is preferably in the shape of a cylinder with rounded ends (a sausage shape), to facilitate its being passed to the intended site.

As just indicated, an ultrasound endoscope is introduced into the patient, passing through the patient's mouth and thence into the stomach. The leading end of the ultrasound endoscope, instead of being allowed to exit the stomach through the pylorus, is directed to the stomach side of the site for the anastomosis. The situation at the anastomosis site is now substantially as shown in FIG. 1 of the drawings except that, contrary to what is shown in that figure, the leading end of a needle with which the ultrasound endoscope is provided is in a retracted position rather than a forward position.

Figure 1:
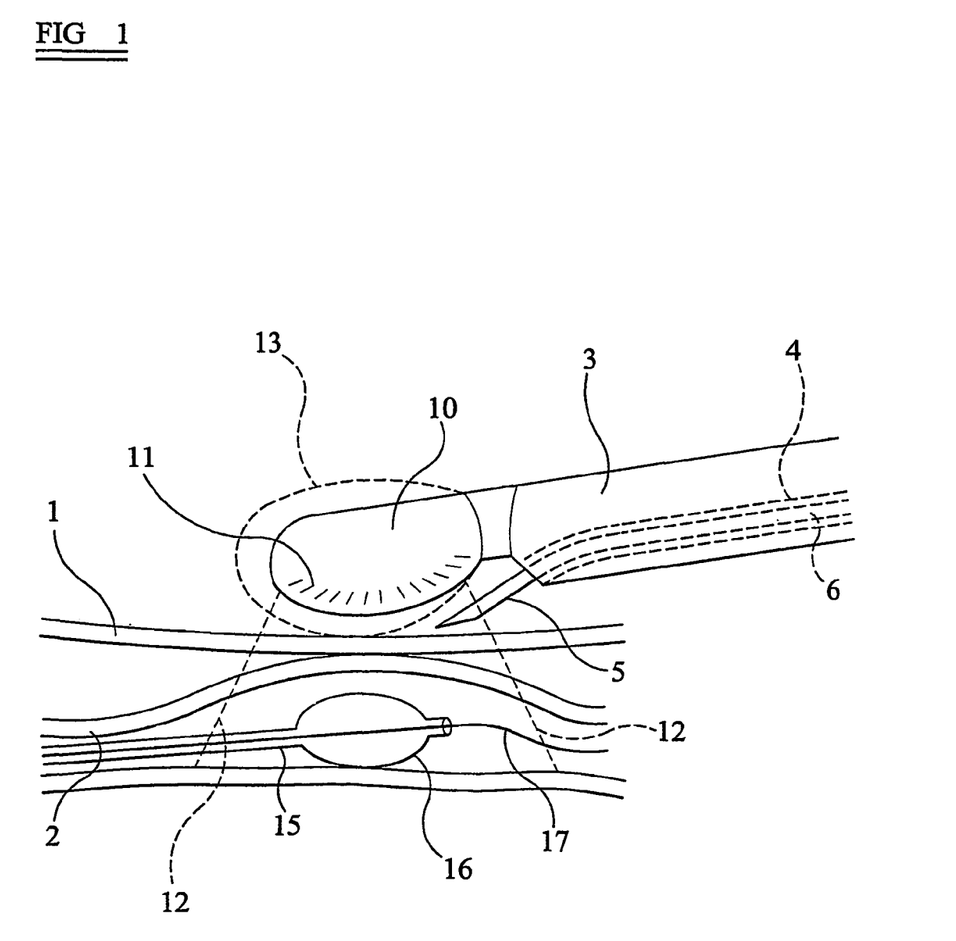
FIG. 1 shows the disposition of the hollow structures which are to be joined by an anastomosis, and the apparatus components for doing so, at the point in time when formation of the anastomosis is about to begin.
Figure 1A:
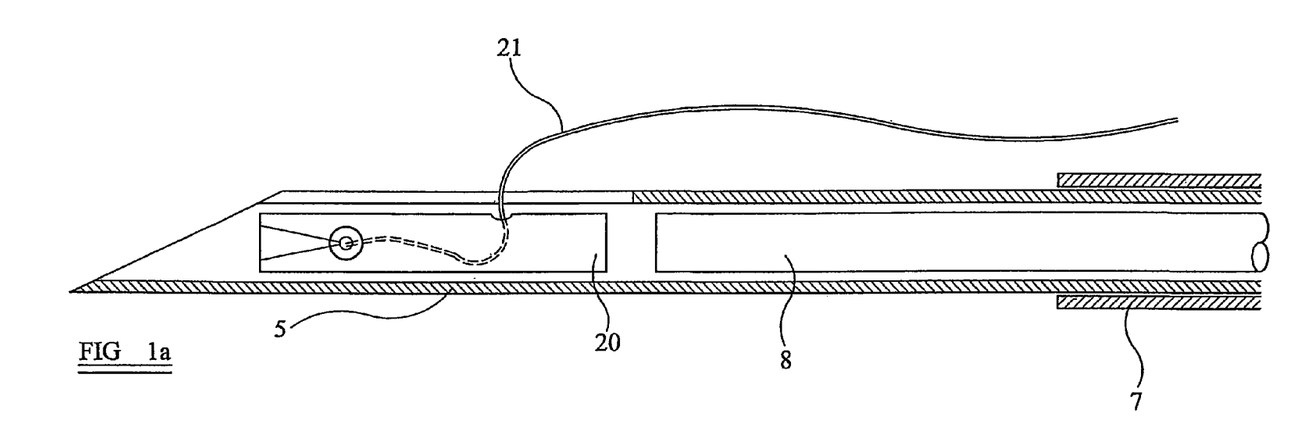
FIGS. 1a and 1b are a vertical section and a plan view, respectively, of part of the apparatus of FIG. 1.
Figure 1B:
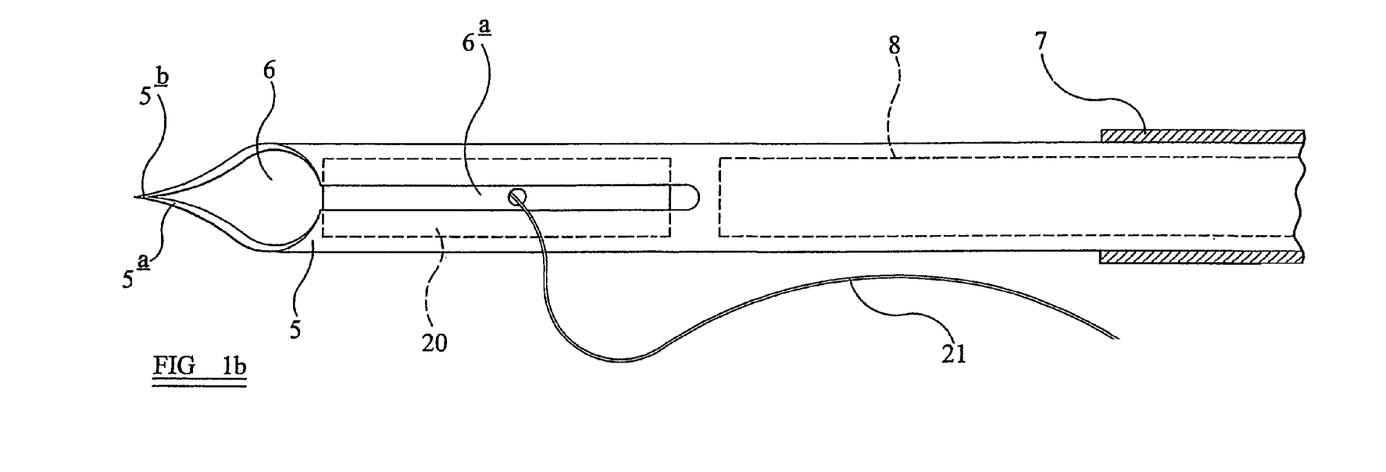

Turning then to FIG. 1 in more detail, this shows a stomach wall portion 1 and a portion 2 of the small bowel. An anastomosis is to be formed between the portions 1 and 2. Positioned adjacent the stomach wall portion 1 is the distal end of a flexible ultrasound endoscope 3 which has a biopsy channel 4. A hollow needle 5 is shown extending from the outlet of the biopsy channel. The endoscope is provided, in known manner, with forward viewing optics adjacent the outlet of the biopsy channel, for viewing the area in front of the biopsy channel. FIGS. 1a and 1b show details of the tip portion of the hollow needle 5. As shown there, it has a bevelled leading portion 5a, terminating in a sharp point 5b. The interior of the needle (which is basically in the form of a hollow cylinder) communicates with the exterior via a forward opening 6 and a longitudinal slot 6a which communicates with the forward opening 6. The needle is longitudinally movable with respect to a sheath 7, and the sheath is itself movable along the biopsy channel of the endoscope 3. A pusher 8 is longitudinally movable within the hollow interior of the needle, and the purpose of the pusher is described further below.

At its extreme distal end the endoscope carries an ultrasonic detector 10, which preferably has a so-called linear detector array 11. This detector array gives a field of view which is indicated by the broken lines 12 in FIG. 1. In order to improve the image produced by the ultrasonic detector 10 it may be surrounded by a balloon, indicated by a broken line 13, with the balloon being filled with water or other liquid. However, this may not be necessary if the user of the endoscope is able to gain sufficiently good contact directly between the ultrasonic detector 10 and the stomach wall portion 1.

Within the small bowel is a balloon catheter, as mentioned above, the balloon being denoted by reference numeral 16 and the catheter itself by reference numeral 15. The guide wire along with the balloon catheter has been introduced is denoted by reference numeral 17. Optionally, the exterior surface of the balloon may be covered with a reticulated sheath 22 (shown in FIG. 2 but not in FIG. 1), or some other material with similar relevant properties, for a purpose which is further described below. To assist in locating the tip of the endoscope 3 and the balloon 16 immediately opposite one another at the anastomosis site, the catheter may be provided with a further channel, in addition to that used for inflating the balloon, through which a medium such as aerated water may be introduced, which is readily detected by an ultrasonic detector.

As shown in FIGS. 1a and 1b a tag 20 is initially positioned adjacent the distal end of the hollow interior of the needle 5. The tag may be made for example, of a surgically acceptable metal. The tag has a thread 21 extending to the exterior of the hollow channel and thence along a path which lies outside the endoscope but is approximately parallel thereto, and so out of the mouth of the patient. In an alternative embodiment (not illustrated) the thread may pass through a channel of the endoscope itself.

Figure 2:
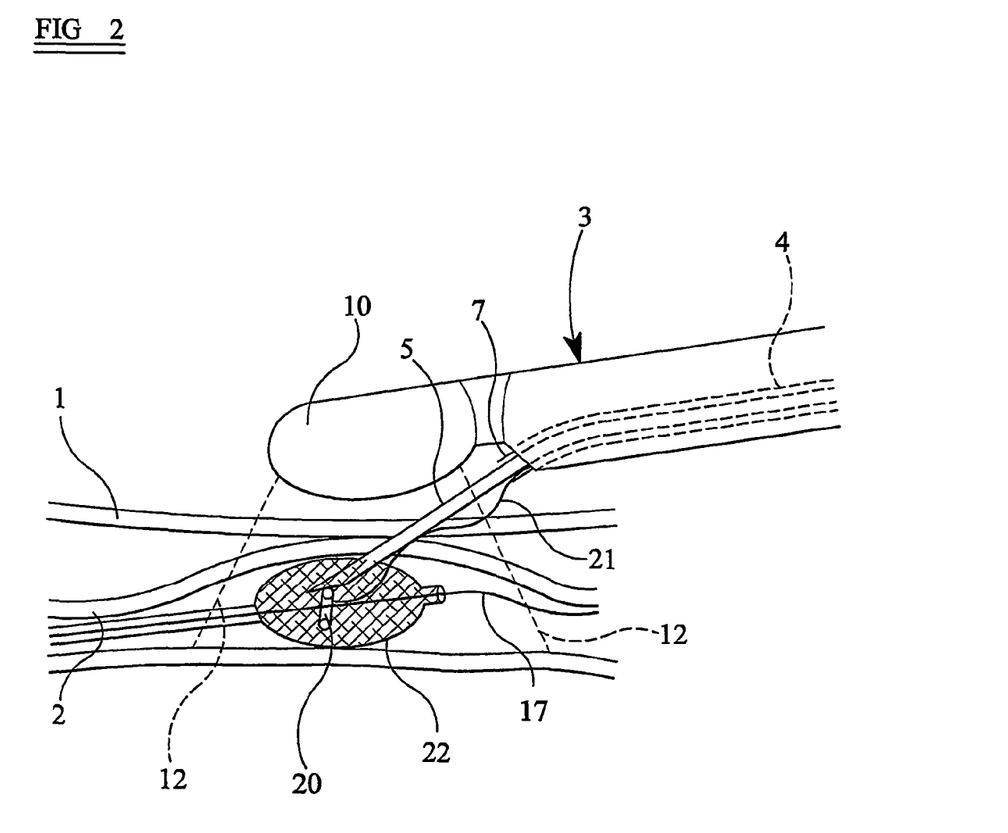
FIG. 2 is a view corresponding to FIG. 1 but taken at a later point in time.

When it is desired to commence formation of the anastomosis, the hollow needle 5 is pushed through the stomach wall portion 1, and thence through the adjacent small bowel portion 2, so that it enters the balloon 16. When the needle enters the balloon it will permit the fluid therein to escape, and the balloon will deflate at least gradually. One way of confirming that the needle has successfully penetrated the balloon is to provide means for sensing the pressure of fluid in the balloon, which should detect a pressure drop at the time of penetration. Another possibility is to inject a contrast medium through the needle after forward movement of the needle has taken place, and confirming its presence in the balloon by imaging the balloon. Once the needle is in the balloon, the tag 20 is expelled from the end of the hollow needle by the pusher 8. This is the stage which is shown in FIG. 2. The purpose of having the optional reticulated sheath 22 is to provide something which will catch the tag in the event that the needle 5, instead of entering the interior of the balloon 16, ends up adjacent the exterior of its side wall. The needle is then withdrawn into the sheath 7, which itself is then withdrawn into the biopsy channel 4 of the endoscope 3.

The balloon catheter is then withdrawn along the same path as that along which it was introduced. In so doing it pulls the tag 20 with it, and that in turn pulls the thread 21 behind it. Eventually a point is reached where the balloon 16, with the tag 20 therein, emerges through the mouth of the patient, at which point the tag, can, if desired, be cut off. The ultrasound endoscope is then withdrawn from the patient also. At this point a situation has been reached where there is a loop of thread which passes in through the mouth of the patient, through the adjacent portions of the stomach wall and small bowel into the interior of the small bowel, back into the stomach via the pylorus, and thence once more out through the patient's mouth. It may be convenient for one or both end portions of the thread to be distinctively coloured, so that the surgeon can be sure as to which end is which.

It is now possible to form an anastomosis using, for example, a device of the type described above in which there are two mushroom-shaped buttons. To assist understanding of the process, an anastomosis button device is shown diagrammatically in FIG. 9. This comprises a pair of buttons 130, 131 each having a central aperture 132, 133 respectively, with a pin 134 passing through both apertures. The pin has a head 135, and a compression spring 136 bears between the head 135 and the adjacent button 130. For ease of illustration the buttons 130 and 131 are shown spaced apart, but it is to be understood that, in the configuration shown in FIG. 9, the spring 136 would in fact force them together. The portion of the pin 134 remote from the head 135 has circular ratchet teeth 137 formed thereon. A U-shaped pawl 138 is mounted in the button 131, and the base of the is the portion which is visible in the illustration of FIG. 9. The arms of the extend past opposite sides of the portion of the pin which is provided with the ratchet teeth 137, and the arms, being formed of a resilient material, e.g. of metal, bear against the ratchet teeth and engage them.

Figure 9:
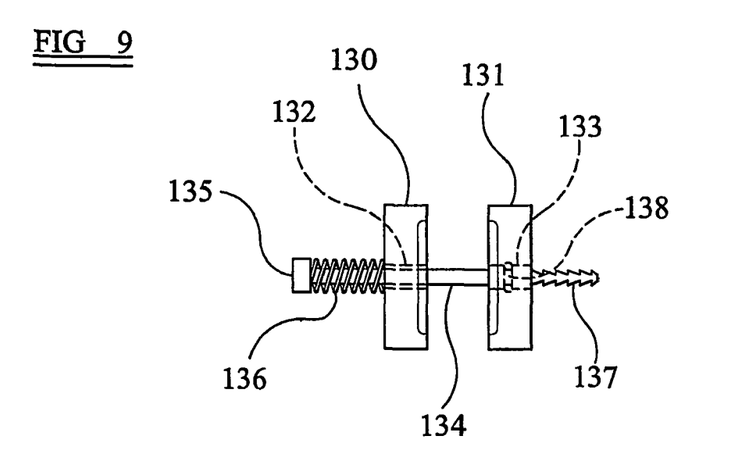
FIG. 9 shows a button device for forming an anastomosis.

To enable the device of FIG. 9 to be used to form an anastomosis under the circumstances described above, the button 131 is detached and the remainder of the device is attached to the thread end which leads via the pylorus to the small bowel. The surgeon then pulls on the other thread end, which causes the anastomosis-forming device to be drawn in through the patient's mouth and eventually to the small bowel side of the site where the anastomosis is to be formed. Continued pulling on the thread causes the ratchet-containing portion of the pin 134 to pass through the adjacent wall portions 1 and 2, so as to protrude into the stomach. The button 131 is then threaded onto the other thread portion extending from the patient's mouth, that thread portion being passed through the aperture 133. The button 131 is then caused to slide down the thread, for example by using a conventional endoscope, with the thread passing up a channel in the endoscope. When the button 131 reaches the protruding portion of the pin 134, continued pushing on the introducing device (e.g. endoscope) pushes the button 131 onto the pin 134, causing the pawl 138 to engage with the ratchet teeth. Assuming that the device for introducing the button 131 is an endoscope, the viewing optics with which it is provided can be used to enable the surgeon to ensure alignment between the button 131 and the end of the pin 134. The anastomosis device of FIG. 9 is therefore now, in effect, reassembled at the anastomosis site, and the buttons 130 and 131 can exert a force on the tissue between them to produce an anastomosis. This is as described in the above-referenced paper by Swain and Mills.

It is to be understood that instead of using buttons of the type described above, other devices could be used to apply the requisite compression to the tissue, for example one could use an appropriately modified prior art magnetic device.

One possible modification to the procedure described above would be to use the ultrasound endoscope to introduce the balloon catheter as well as the tag, with the ultrasound endoscope being kept in the stomach during both introductions.

The method described above with reference to FIGS. 1, 1a, 1b and 2 assumes that it is possible to gain access to both sides of the anastomosis site. Sometimes, however, this will not be possible. For example, if, in the condition illustrated in FIG. 8, the tumour completely blocked the small bowel the anastomosis site would only be accessible from the stomach side. Also, one of the organs involved in the anastomosis may be one which, even in its normal condition, is not accessible to a catheter, for example the gallbladder. One way of addressing this problem is by means of the embodiment shown in FIGS. 3a, 3b and 4a to 4e.

Figure 3A:
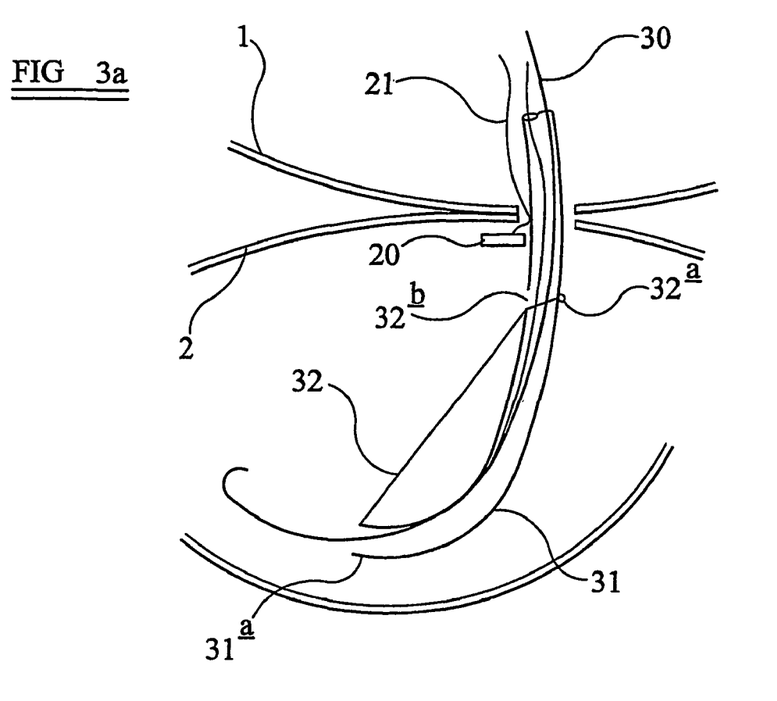
FIGS. 3a and 3b show two stages in the use of a device for holding the two tubular structures together prior to the formation of an anastomosis.
Figure 3B:
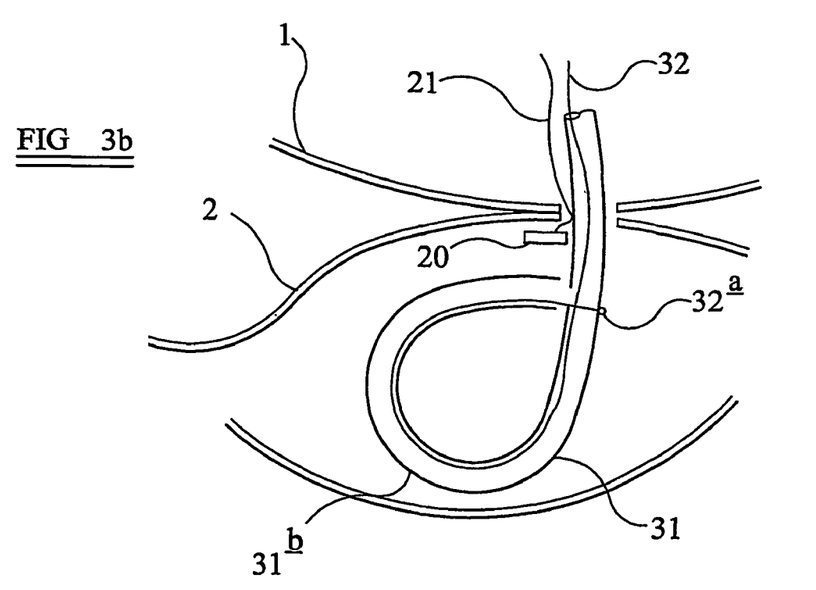

Turning first to FIG. 3a, this illustrates a situation which has been reached by using an endoscope to insert a tag 20, with its thread 21, using an endoscope which is the same as, or similar to, the endoscope 3 shown in the previous embodiment. The pusher 8 is then withdrawn from its channel and a guide wire is passed from the patient's mouth, through the channel previously occupied by the pusher, and through the hollow needle 5, into the small bowel. The hollow needle is then withdrawn, leaving the guidewire in place. An elongate member in the form of a catheter 31 is slid down over the guide wire 30 until it reaches the illustrated position. The tip 31a of the catheter 31 is preferably formed of a material with relatively low friction (it may, for example, be made of a metal such as stainless steel), so as to make it easier to introduce the catheter. A thread 32 runs down inside the catheter 31, emerges from the tip 31a, and has its leading end passing through an aperture 32b in the body of the catheter, and secured to the body at 32a.

An anastomosis is then formed as follow. Firstly, the guide wire is preferably withdrawn at least sufficiently so that its tip no longer protrudes from the end of the catheter. Then the surgeon exerts an upward force on the portion of the thread 32 emerging from the patient's mouth. This causes the distal portion of the catheter 31 to form a loop, as indicated by reference numeral 31b in FIG. 3b. As an alternative to what is described, the thread 32 could run downside the catheter as far as aperture 32b emerge from the inside of the catheter through the aperture 32b, and be secured to the catheter at or adjacent the tip 31a. Such a thread would form a loop in the same way as that shown in FIGS. 3a and 3b.

The following stages of the procedure are shown with reference to FIGS. 4a to 4e, and involve the use of a bell-shaped member 40 which, because it acts like one of the buttons 30, 31 in FIG. 9, will be referred to below as a bell-shaped button. The button 40 is approximately elliptical as viewed in longitudinal section, as can be seen in FIG. 4e, and it is the major access of the ellipse which can be seen in each of FIGS. 4b, 4c and 4d.

Figure 4A:
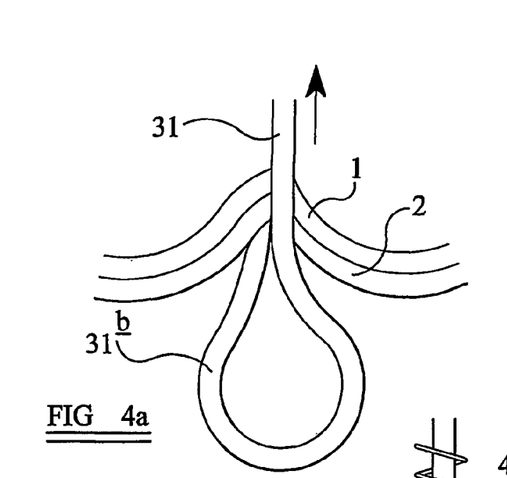
Figure 4B:
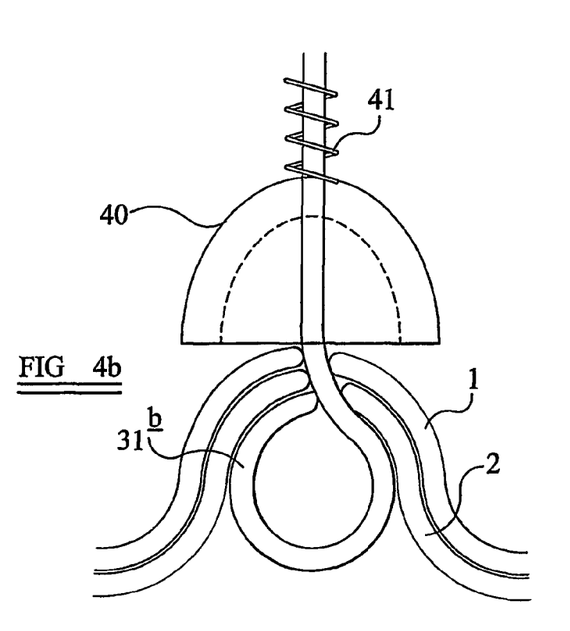
Figure 4C:
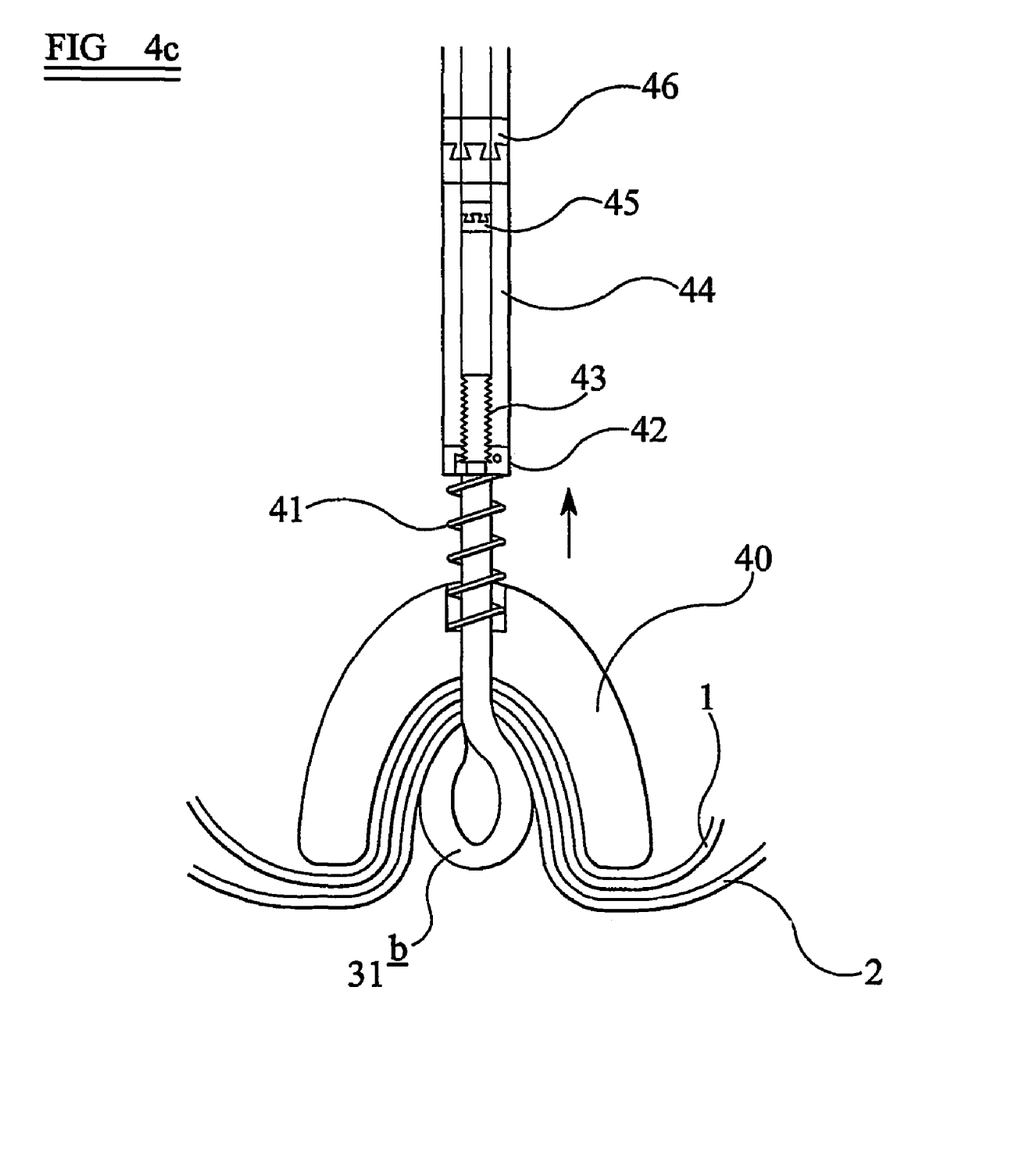
Figure 4D:
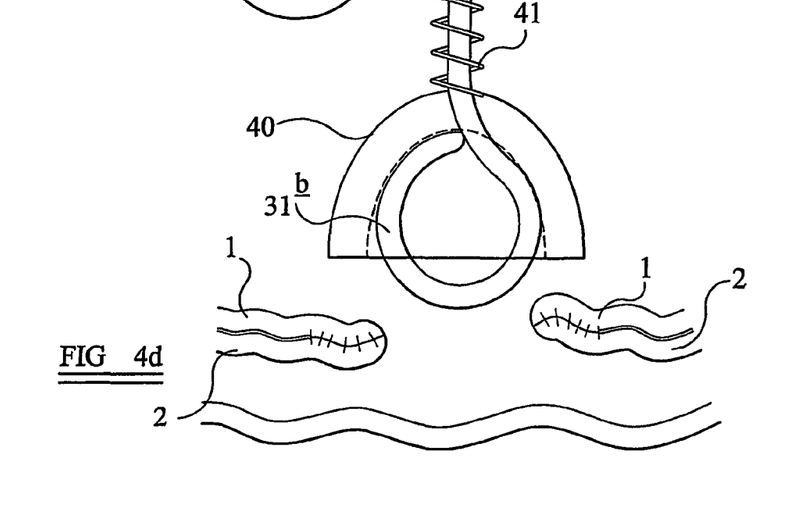
Figure 4E:
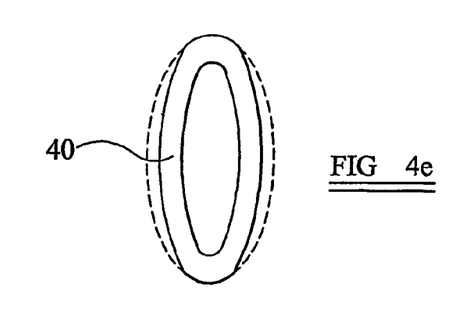
FIG. 4e is a cross sectional view through a bell-shaped button which constitutes another of the components used in FIGS. 4a to 4d.

As indicated in FIG. 4a, an upward force is exerted by the surgeon on the catheter 31, so that the loop 31b urges the tissue portions 1 and 2 upwardly at the site intended for the anastomosis. The bell-shaped button 40 has a central aperture, and this enables it to be passed down over the catheter 31 to the anastomosis site, as shown in FIG. 4b. Further downward movement of the bell-shaped button 40 brings it to the position shown in FIG. 4c, at which the tissue portions 1 and 2 are compressed between the button 40 and the loop 31b. As shown in FIG. 4c (and in FIG. 4b) the button 40 carries a compression spring 41. This corresponds in function to the spring 136 in FIG. 9. Thus, the lower end of the spring bears against the button 40 and the upper end of the spring bears against a locking member 42 mounted on the distal end of an upper tubular member 44. The member 42 has an internal pawl engaging a ratchet tooth member 43 which faces outwardly from the exterior surface of the catheter 31. FIG. 4c also shows release mechanisms 45 and 46 which respectively releasably connect the catheter 31 to a continuation thereof, in a direction towards the patient's mouth, and releasably connect the tubular member 44 to a continuation thereof (though in practice release mechanism 46 may be unnecessary). The nature of these release mechanisms is described below with reference to FIGS. 7a and 7b. In effect, the loop 31b provides a second button to complement the button 40. As with conventional anastomosis buttons, the effect is eventually as shown in FIG. 4d, with the tissue portions 1 and 2 being joined together, and an opening being formed where they were under compression. The catheter 31 can then be withdrawn, carrying the button 40 with it.

In a modification of the embodiment shown in FIGS. 3a, 3b and 4a-4e, the dome-shaped button 40 could be replaced by a hollow member of some other shape, e.g. ogival. Also, instead of being rigid it could be of a flexible material, preferably an elastic material.

Figure 5A:
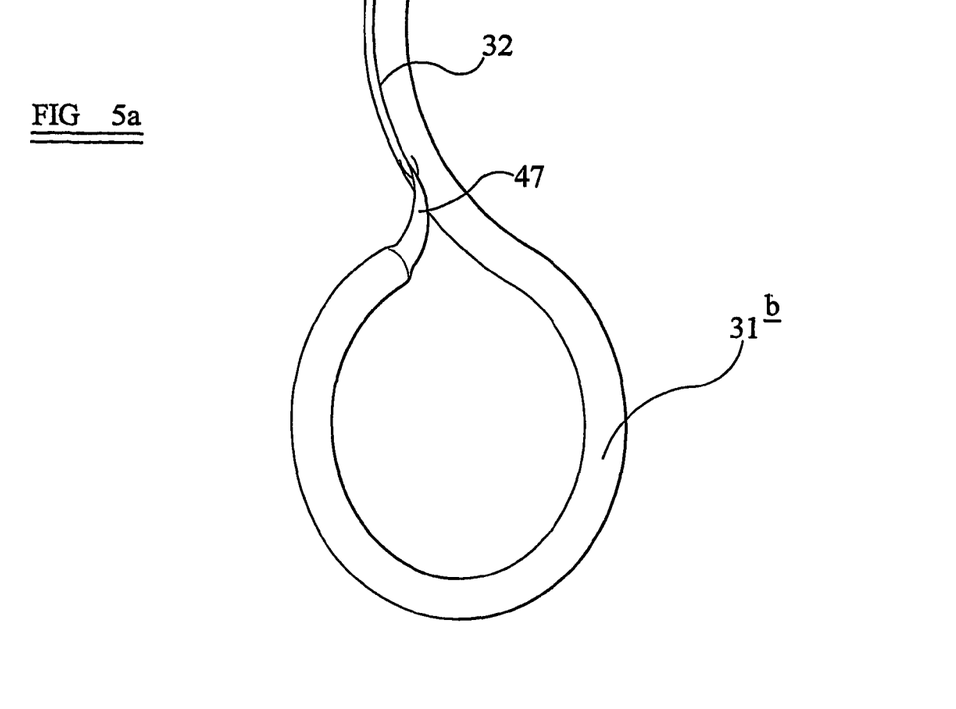
FIGS. 5a and 5b show a modification of the loop-forming device employed in FIGS. 3a and 3b and in FIGS. 4a to 4d.
Figure 5B:
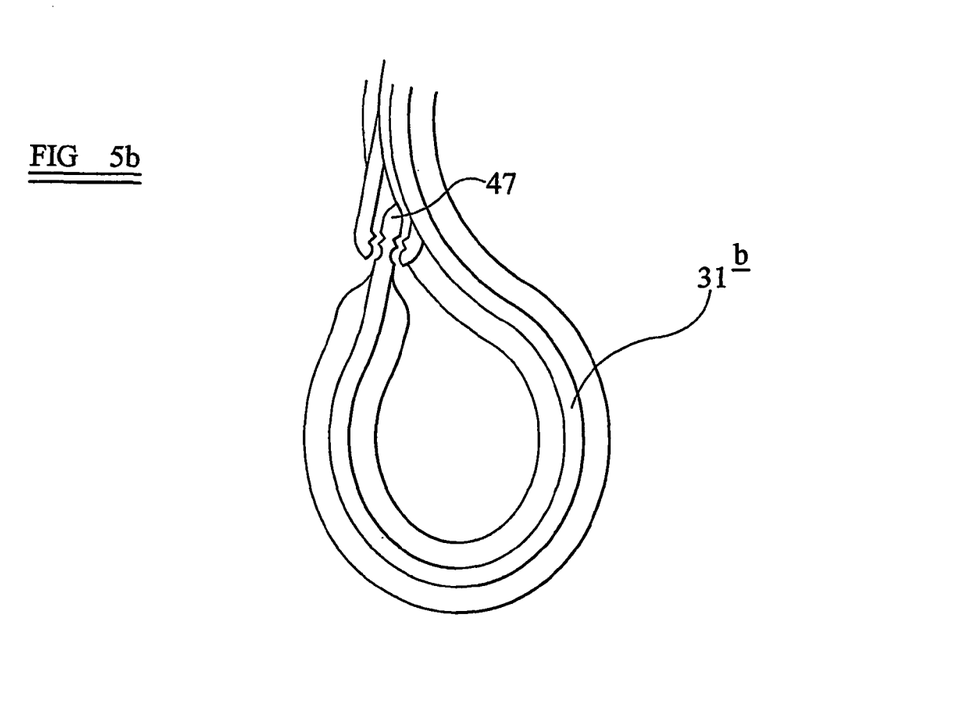

FIGS. 5a and 5b show a modification of the catheter 31 used in the preceding embodiment. In this modification the catheter is provided with a locking tip 47 which is adapted to engage with a complementary structure in the wall of the catheter when the loop 31b is formed. This avoids the need to maintain tension on the thread 32 to maintain the loop 31b.

An alternative to the locking mechanism shown in FIGS. 5a and 5b would be to insert a locking member, which might, for example, be conical in shape, within the catheter, above where the catheter of FIGS. 5a and 5b has a locking tip, to clamp the thread 32 against the internal wall of the catheter.

Figure 6:
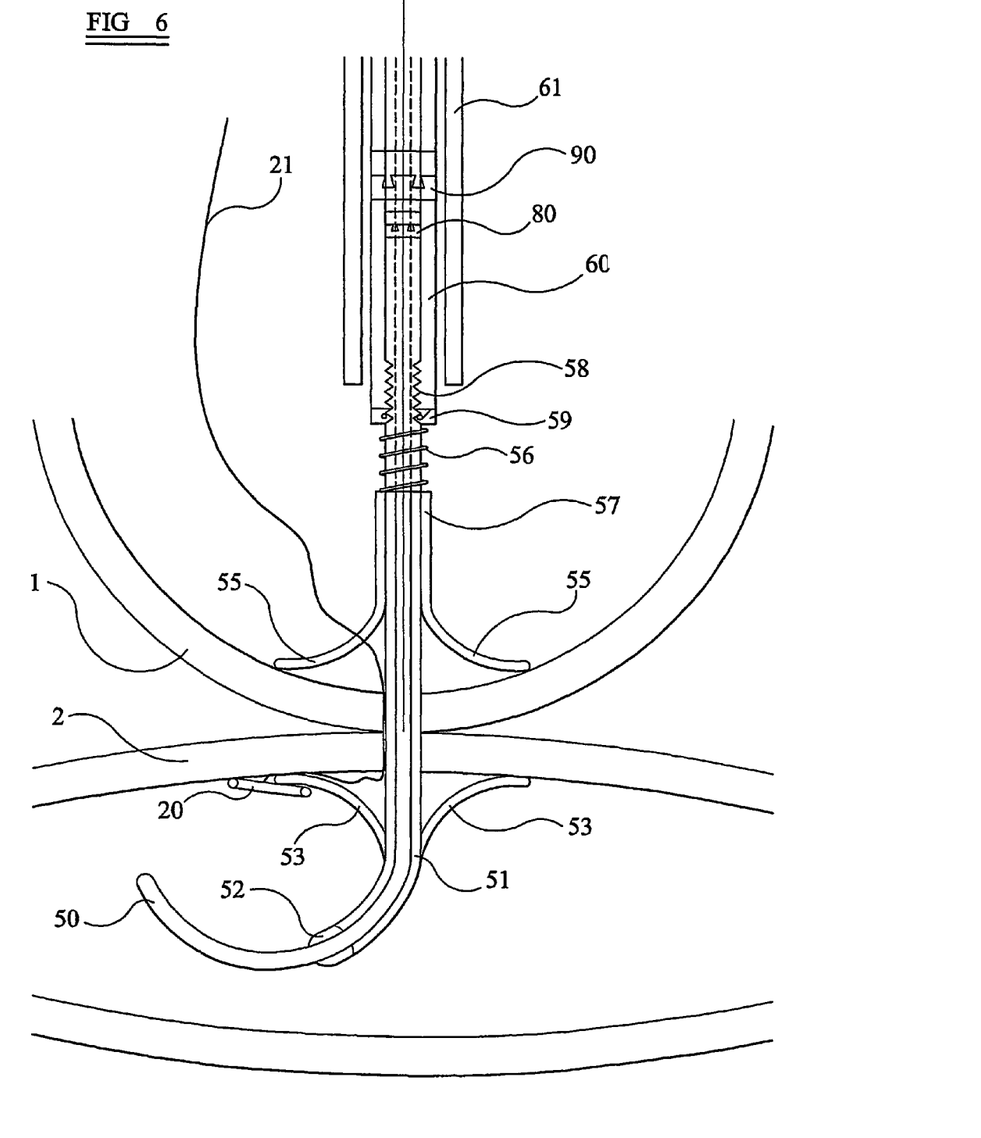
FIG. 6 shows an alternative device to that illustrated in the earlier figures, for forming an anastomosis.

FIG. 6 shows an alternative device for forming an anastomosis. This too is capable of being used when there is access to only one side of the anastomosis site. Its operation assumes that a tag 20, with its thread 21, has previously been introduced as described with reference to FIGS. 1 and 2, or by some similar method. In the condition illustrated in FIG. 6 the hollow needle has been withdrawn from the endoscope, but the endoscope is still in position. The method illustrated in FIG. 6 also assumes that a guide wire has been provided, the wire being denoted in FIG. 6 by reference numeral 50. This wire is put in position by the same procedure as described above with reference to FIGS. 3a and 3b, so that it runs down the biopsy channel 4 of the endoscope, through the tissue portions 1 and 2, beside the thread 21, and terminates on the remote side of the anastomosis site. Preferably the guide wire 50 has a soft tip, and increases in stiffness in a direction away from the tip.

A flexible plastic catheter 51 is passed down the biopsy channel, over the guide wire 50, until its tip 52 is positioned as shown in FIG. 6. The tip is preferably made of a low friction material, for example stainless steel. The distal portion of the catheter 51 carries a plurality of flaps 53 which are positioned on the exterior of the catheter. The flaps 53 may be realised as distinct members (as shown), or they may be formed integrally with the catheter 51. While the catheter is being pushed down the biopsy tube the flaps 53 lie approximately parallel to the catheter, but when they emerge on the remote side of the tissue portion 2 they spring outwards to assume the positions shown in FIG. 6. Preferably there are four such spring flaps, two being located as illustrated, and two further flaps being positioned at 90° to the illustrated flaps, i.e. they extend respectively into and out of the plane of the paper. A second flap-carrying member, in the form of a tube 57 is slid down over the catheter 51 until its spring flaps 55 come to bear against the proximal side of the tissue portion 1. As in the case of flaps 53, the flaps 53 may be realised as distinct members, or they may be formed integrally with the catheter 51. The flaps 55 are urged against the tissue portion 1, so causing tissue to be compressed between the flaps 53 and 55, by a spring 56, the lower end of which bears against the upper end of the tube 57, and the upper end of which bears against a pawl member 59. The catheter 51 carries a ratchet tooth member 58 (or has teeth formed thereon), of similar construction to the member 43 described above, and this is engaged by an internal pawl in the pawl member 59 at the lower end of a tubular member 60, thereby to maintain the above compression. The upper part of the device of FIG. 6 is surrounded by a catheter 61.

The spring flaps 53 and 55 thus perform the compression function which, in the first of the illustrated embodiments, is performed by the buttons 30 and 31, and result in an anastomosis being formed.

Figures 7A, 7B:
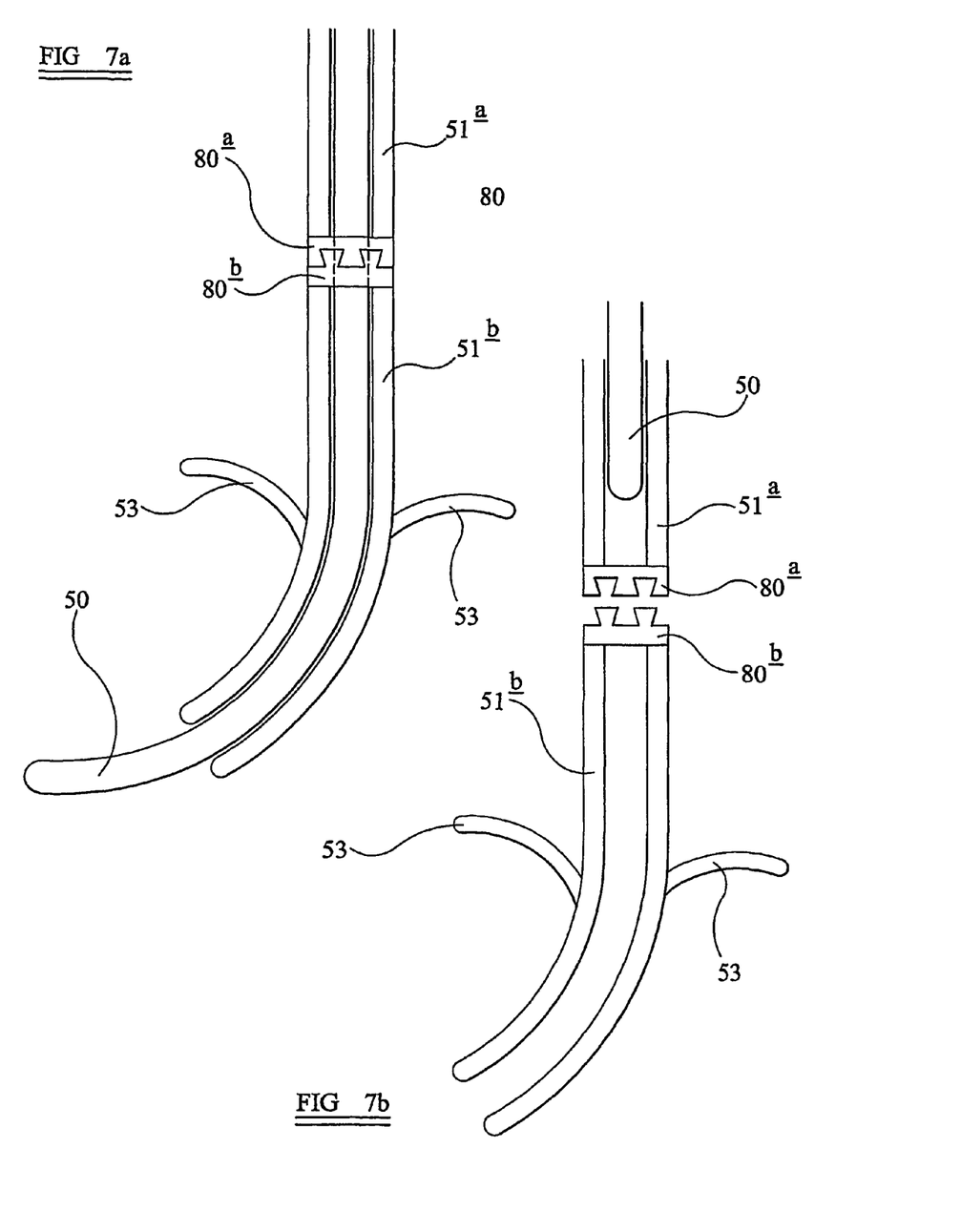
FIGS. 7a and 7b show successive stages in the use of a release mechanism which may be incorporated in some of the previously illustrated embodiments.

FIG. 6 indicates the presence of a release mechanism 80, and an example of this is shown in more detail in FIGS. 7a and 7b. (FIG. 6 also shows a similar release member 90 in the tubular member 60, though in practice this may be unnecessary. Indeed its presence may actually make release more difficult to achieve, in which case it is preferably omitted). As shown in FIGS. 7a and 7b, the catheter 51 has a main upper portion 51a connected to a lower portion 51b by the release mechanism 80. In the illustrated embodiment this is formed by a dovetail joint, with one dovetail member 80a being connected to the main catheter portion, and the complementary dovetail portion 80b being connected to the lower catheter portion 51b. In the drawing, the portion 80a is shown as being a female member, and the portion 80b is shown as being a male member, but of course these could be reversed. The portions 80a and 80b engage one another quite loosely, but are unable to separate from one another as long as the guide wire 50 is in position, as it is in FIG. 7a. The guide wire passes through an aperture in the centre of the members 80a and 80b. However, when the guide wire is withdrawn to the extent shown in FIG. 7b the members 80a and 80b are free to separate from one another, and since they are only loosely connected they will do so of their own accord. It is then possible for the surgeon to withdraw the upper portion of the catheter, with the guide wire, completely from the patient, leaving the lower portion in position and passing through the anastomosis site. The lower portion can thus then act as a stent to help keep the anastomosis open and ensuring drainage. It should be noted that instead of dovetail members the interlocking portions could be of any other shape which prevented them from being separated in the position of FIG. 7a but permitted them to be separated in the position of FIG. 7b. Also, an alternative construction can be envisaged in which, instead of keeping the portions 80a and 80b together by a guide wire, they could be kept together by an external catheter.

In a modification of the embodiment shown in FIG. 6 the spring flaps 55, but not the spring flaps 53, are replaced by a single conical member which, like the flaps 55 in FIG. 6, is urged against the tissue portion 1 by a spring.

Figure 10:
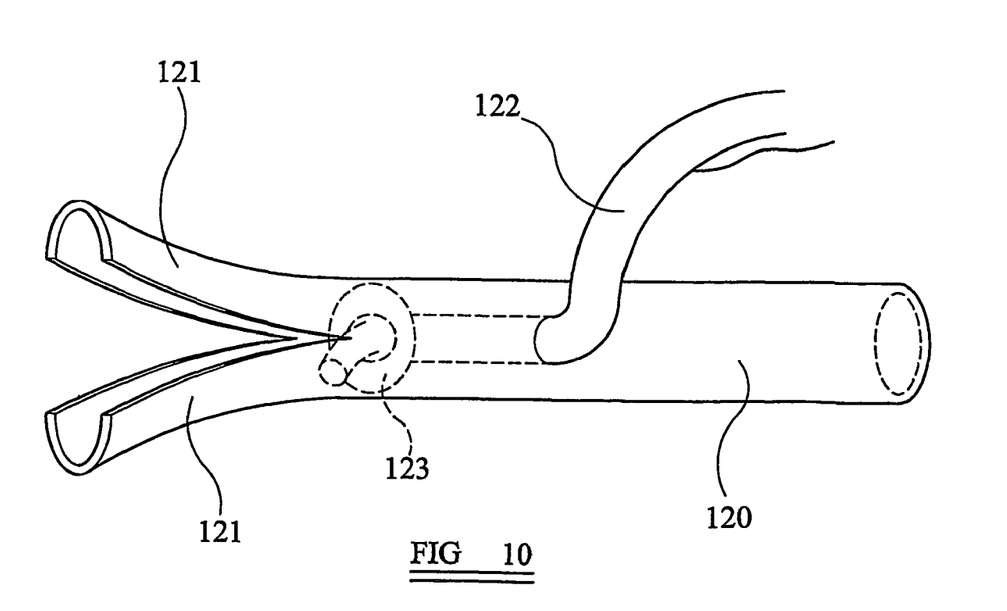
FIG. 10 shows a modified form of tag for use in the invention.

A number of further modifications can be made to various devices described above. One of these is illustrated in FIG. 10, which shows a modified tag 120 which is made of a hollow cylinder of resilient material, and which has split end portions 121 which, when no force is applied to the tag, adopt the positions shown in FIG. 10. The thread 122 is attached to the tag 120 by passing the end through an aperture therein and tying a knot 123 in the end of the thread. Alternatively, the thread 122 could be crimped in place. When the tag 120 is inside the hollow needle the end portions 121 are urged together by the interior surface of the needle. This creates a frictional force between the tag and the needle which helps to ensure that it cannot accidentally fall out of the needle. To eject the tag from the needle requires the pusher to exert a force on the tag sufficient to overcome the frictional force.

If desired, the needle tip, tag, thread and anastomosis button (or the equivalent of those buttons) may be roughened in order to improve the extent to which they reflect ultrasound. Of course, these components cannot be made too rough, or there may be difficulty in inserting and/or removing them and, possibly, injury to the patient. It may be desired to use X-ray imaging, preferably in real time, to supplement or replace some of the other imaging techniques referred to above. In that case it may be desirable to improve the visibility to X-rays of components, such as plastic catheters, by marking them, at the tip or elsewhere, with a heavy metal coating.

Another modification, which may be employed where the tag is left in place during the formation of the anastomosis (e.g. as in the methods of FIGS. 3a to 6) is to make the tag of an absorbable material. This may be useful where the hollow structure within which it is located is one which is not externally accessible, for example the gallbladder. Although the tag should be capable of being removed at the end of the procedure, it may not be, for example if an anastomosis fails to form, and a metal tag remaining in the gallbladder could be a nidus for infection or stone formation.

Yet another modification in relation to the tag is for it to be of spiral or angulated shape, enabling it to spread the load exerted by the tag on the tissue portion 2.

It is also noted that the tag, instead of being a completely separate entity mounted in the needle tip, could itself constitute a detachable needle tip (with a thread attached thereto).

Another possibility in relation to the use of tags is to arrange for a plurality of tags to be dispensed successively from a hollow needle into the second hollow structure. Such a plurality of tag's might then be used to form one side of the anastomosis device, i.e. replace the button or the like on that side of the anastomosis site.

One modification as regards the pusher is that, provided its tip were appropriate, it could be used as a guide wire, once it has fulfilled its function as a pusher, eliminating the need for a separate guide wire at that stage at the location where the pusher was able to provide it.

Figures 11, 12:
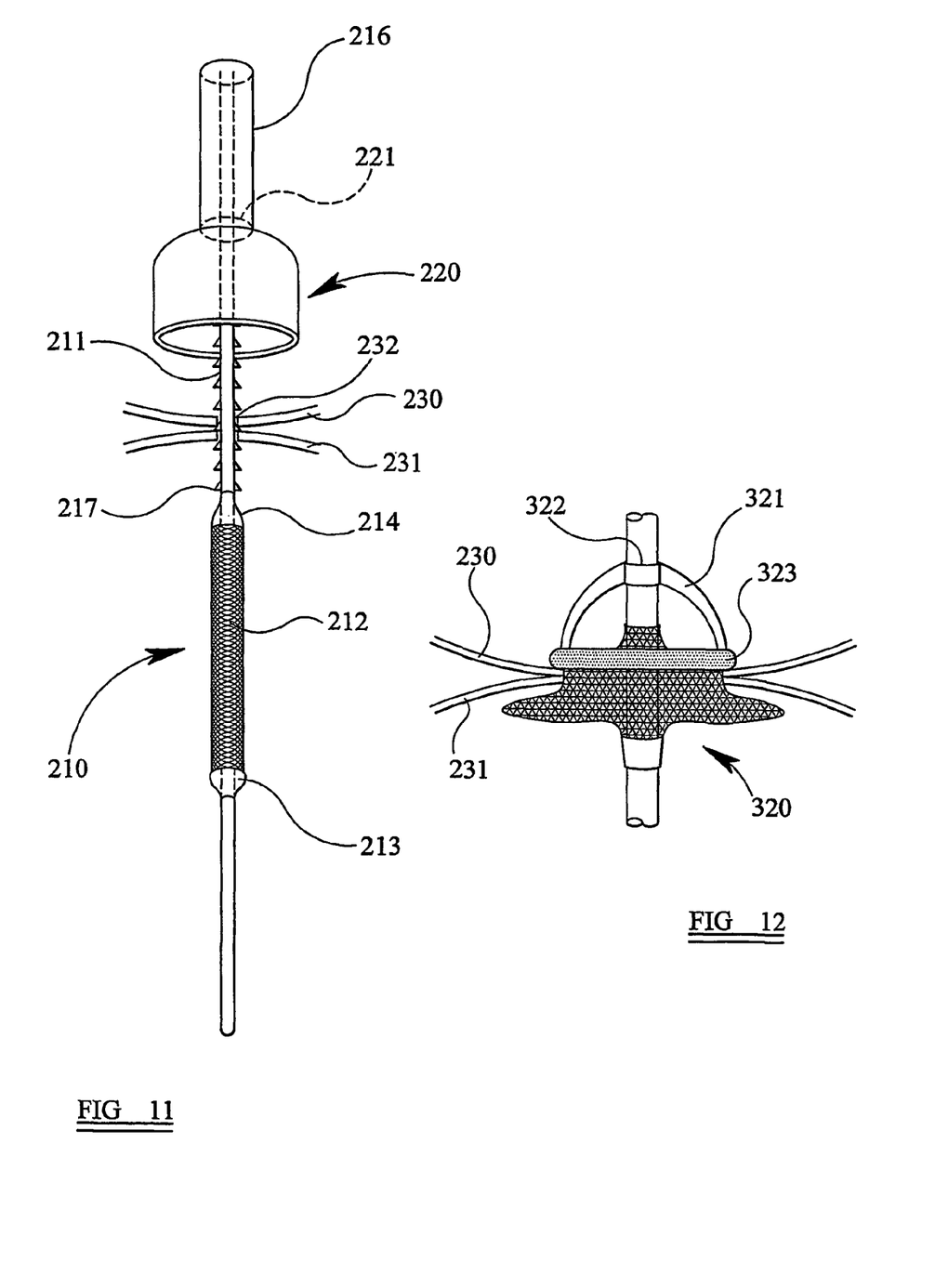
FIG. 11 shows an anastomosis forming device using a braided sheath.
FIG. 12 shows a modification of part of the device of FIG. 11.

FIGS. 11 and 12 show, in two variants, a particular form of anastomosis device which may be used. The device shown in FIG. 11 comprises a first element 210 which comprises a carrier member, in the form of a catheter 211, which runs through a braided sheath 212. Such sheaths may be of a design similar to, or the same as, braided sheaths which are used in electrical work, provided, of course, that the material of the sheath is surgically acceptable. At one of its ends the sheath 212 is fixed to the catheter 211 by a fixing element 213. The other end of the sheath is attached to a collar 214 which is slidable on the catheter 211. Ratchet teeth 217 are formed on the exterior of a portion of the catheter 211, for a purpose described below.

The device further comprises a second element in the form of an inverted cup 220, the cup having an aperture 22i in the base thereof, the aperture being large enough to permit the catheter to move through it.

In use the element 220 is positioned on one side of two layers of tissue 230, 231, between which the anastomosis is to be formed. A hole 232 has previously been formed through the two layers, and one end of the catheter 211 passes through this hole, through the aperture 221 in the cup 220, and up inside a hollow member 216 (for example the distal end of an endoscope). The remainder of the element 210 is on the opposite side of the tissue layers.

To form the anastomosis the catheter 211 is drawn upwardly (as viewed in the drawing), while the cup 220 is pushed downwards by the tubular member 216, thus drawing the fixing element 213 upwardly, and, with it, the lower end of the sheath 212. This action causes the sheath to bulge outwardly, thus bringing the tissue layers 230, 231 into conformity with the interior surface of the cup 220. Simultaneously, the ratchet teeth 217 engage with the periphery of the aperture 221. The teeth permit the catheter ro move upwardly through the aperture 221 and prevent movement in the opposite direction. The tissue layers are thus compressed between the cup and the sheath. The pressure is maintained long enough for an anastomosis to be formed, after which the device can be removed.

Various modifications can be made to the structure described above. For example, the cup may be reduced to a skeletal form 320, as indicated in FIG. 12, where it is shown as consisting of ribs 321, whose upper ends define an aperture 322, and a ring 323 connecting the lower ends of the ribs. FIG. 12 shows the tissue layer 230 in contact only with the ring (the layers 230 and 231 do not enter the interior of the cup 230). It is to be noted that in the case of cup 220 this too could operate by having only the lower rim of the cup in contact with the tissue layer 230, with the layers 230 and 231 not entering the interior of the cup.

The invention claimed is:

1. A method of forming an anastomosis joining a first tissue layer forming a wall of a first hollow region and a second tissue layer forming a wall of a second hollow region, comprising the steps of:
   passing a tag from the first hollow region to the second hollow region through the first and second tissue layers, without requiring creation of an external opening, the tag having a trailing portion extending into the first hollow region,
   pulling the trailing portion to draw the tissue layers towards one another and into face-to-face relationship with one another,
   introducing a first component of an anastomosis-forming article into the first hollow region, and a second component of an anastomosis-forming article into the second hollow region, the second component of said article being introduced into the second hollow region through the first and second tissue layers, and
   after introducing the first and second components of the anastomosis-forming article, moving the first and second components towards one another to compress the first and second tissue layers therebetween, and cause the tissue layers to be welded to one another by a consequent ischemia, so as to form an anastomosis communicating the first and second hollow regions.

2. A method according to claim 1, wherein the tag is removably carried by the step of passing a tag from the first hollow region to the second hollow region by passing a needle from the first region to the second region by penetrating said tissue layers.

3. A method according to claim 1, wherein the step of introducing the said second component into the second hollow region comprises providing an elongate member having a proximal region and a distal region terminating in a distal end, inserting the distal region of the elongate member into the second hollow region in parallel with the trailing portion of the tag, and forming the distal region into a loop, the loop being adapted to act as the said second component.

4. A method according to claim 3, wherein the said elongate member is hollow, and wherein the loop is formed using a thread which runs within the elongate member from the proximal region to the distal region, emerges from the elongate member at the distal end thereof, and runs externally of the elongate member to a location in the distal region of the elongate member where it is secured to the elongate member.

5. A method according to claim 3, wherein the second component of the anastomosis-forming article is a hollow member, open in a direction towards the first component thereof.

6. A method according to claim 3, wherein the distal end of the elongate member is provided with a locking tip, and the locking tip engages the wall of the elongate member when the loop is formed.

7. A method according to claim 1, wherein the step of introducing the said first component into the first hollow region and the second component into the second hollow region comprises providing first and second elongate coaxial members, longitudinally movable with respect to one another, passing the first elongate member from the first hollow region into the second hollow region, the said first elongate member having wall-engaging means for engaging the wall of the second hollow region to prevent its return to the first hollow region, keeping the second elongate member in the first hollow region, the second elongate member being provided with wall-engaging means to prevent it passing into the second hollow region, the wall-engaging means of the first and second members constituting respectively the said second and first components of the anastomosis-forming article.

8. A method according to claim 7, wherein the said first elongate member runs within the second elongate member.

9. A method according to claim 7, wherein the first elongate member is releasably attached to an introducing article prior to the introduction of the members into the respective hollow regions, and is detached thereafter from the introducing article.

10. A method according to claim 9, wherein the said first elongate member is releasably attached to the introducing article by interengaging portions on a proximal end of the first elongate member and a distal end of the introducing article, engagement of the interengaging portions being maintained only while a wire passes longitudinally through them or a tube passes longitudinally around them.

11. A method according to claim 1, wherein the said first component is a hollow member in the form of a cup comprising a base end and an open end, the open end being open in a direction towards the said second component, and the said second component comprising a sheath, wherein the sheath is moved between an extended position in which its diameter is sufficiently small for it to pass from the first hollow region to the second hollow region, and a contracted position in which its diameter is sufficiently large to prevent it returning from the second hollow region to the first hollow region.

12. A method according to claim 11, wherein the sheath is a braided sheath.

* * * * *